United States Patent
Paskewitz et al.

(10) Patent No.: US 10,618,936 B2
(45) Date of Patent: Apr. 14, 2020

(54) **INSECT, TICK, AND MITE REPELLENT DERIVED FROM *XENORHABDUS BUDAPESTENSIS***

(71) Applicant: Wisconsin Alumni Research Foundation, Madison, WI (US)

(72) Inventors: Susan M. Paskewitz, Madison, WI (US); Mayur K. Kajla, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/176,381

(22) Filed: Oct. 31, 2018

(65) Prior Publication Data
US 2019/0127421 A1  May 2, 2019

Related U.S. Application Data

(60) Provisional application No. 62/579,275, filed on Oct. 31, 2017.

(51) Int. Cl.
| | |
|---|---|
| *A01N 43/56* | (2006.01) |
| *C07K 7/02* | (2006.01) |
| *A01N 43/64* | (2006.01) |
| *C07K 7/56* | (2006.01) |

(52) U.S. Cl.
CPC ............ *C07K 7/02* (2013.01); *A01N 43/64* (2013.01); *C07K 7/56* (2013.01)

(58) Field of Classification Search
None
See application file for complete search history.

(56) References Cited

PUBLICATIONS

Fuchs, S.W. et al (Fuchs), Fabclavines:Bioactive Peptide-poylketide-Polyamino Hybrids from Xenorhabdus, ChemBioChem, 15, 512-516 (2014) (Year: 2014).*

Mayur K. Kajla, Gregory A. Barrett-Wilt, Susan M. Paskewitz Bacteria: A novel source for potent mosquito feeding-deterrents, Science AdvancesJan. 16, 2019 (Year: 2019).*

* cited by examiner

*Primary Examiner* — Thomas S Heard
(74) *Attorney, Agent, or Firm* — Joseph T. Leone, Esq.; DeWitt LLP (57) ABSTRACT

Insect-repellent compositions containing compounds of Formula I:

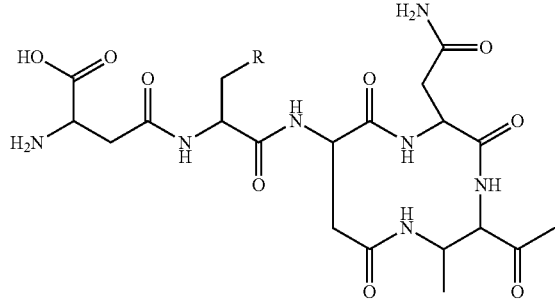

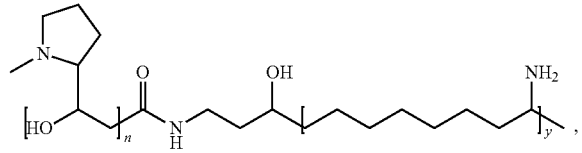

wherein R is a 5-membered or 6-membered carbon-containing ring, having zero, one, two, or three double bonds, and having zero, one, two, or three heteroatoms, wherein the one, two, or three heteroatoms, if present, are selected from nitrogen, oxygen, and sulfur; "x" is an integer from 0 to 5; and "y" is an integer from 1 to 10.

5 Claims, 8 Drawing Sheets

INSECT, TICK, AND MITE REPELLENT DERIVED FROM *XENORHABDUS BUDAPESTENSIS*

CROSS-REFERENCE TO RELATED APPLICATIONS

Priority is hereby claimed to provisional application Ser. No. 62/579,275, filed Oct. 31, 2017, which is incorporated herein by reference.

FEDERAL FUNDING STATEMENT

This invention was made with government support under A1123719 awarded by the National Institutes of Health. The government has certain rights in the invention.

BACKGROUND

Arthropod repellents (referred to generically and in vernacular parlance as "insect repellents") have been in existence since time immemorial. Biting insects, spiders, and other arthropods being what they are, they have been inconveniencing, annoying, and sickening mankind for millennia. It is only in the very recent history of human beings that many arthopods, most notably insects and ticks, were identified as vectors of a host of serious and sometimes fatal diseases, including well known ailments such as malaria, dengue fever, Lyme disease, and West Nile virus, and lesser known ailments such as Chagas' disease and filariasis. Limiting the impact of arthropod bites as a mode of disease transmission is an important, worldwide public health goal. Active ingredients of commercially available insect repellents include N,N-diethyl-3-methylbenzamide (DEET), botanicals, citronella, IR3535, p-Menthane-3,8-diol (PMD, lemon eucalyptus) and picaridin. In the United States, the Environmental Protection Agency's list of ingredients approved for application to human skin include DEET, picaridin, MGK-326, MGK-264, IR3535, oil of citronella, and oil of lemon eucalyptus. DEET has been the most efficacious and broadly used insect repellent for more than 50 years. It has a strong safety record and affords excellent protection against ticks, mosquitoes, and other arthropods. Picaridin, first marketed in Europe in 1998 and in the U.S. in 2005, is gaining market share on DEET because of its low irritation. Also, natural product insect repellents, such as oil of lemon eucalyptus, are becoming more popular among some consumers because they are perceived as "green" and therefore safer than synthetic repellents. However, currently available natural product insect repellents are not as overall effective as is DEET (i.e., based on repellency, duration of repellency, number and types of species affected, etc.) Thus, there remains a long-felt and unmet need for a natural product insect repellent that displays the desired insect-repellent qualities of synthetic insect repellents such as DEET and picaridin.

SUMMARY

*Xenorhabdus* bacteria, which live in symbiotic relationship with entomopathogenic *Steinernema* nematodes, produce secondary metabolites that exhibit antibiotic, insecticidal and cytotoxic activities. Bacterial production of these molecules and their role in *Xenorhabdus*-nematode-insects relationship has been reported; however unique functions such as mosquito deterrence have not been investigated. In the present invention, crude supernatants from *Xenorhabdus* bacterial cultures were screened for repellency against mosquitoes. An in vitro blood feeding assay was used to measure repellency. It was found that compounds produced by *Xenorhabdus budapestensis* (Xbu), exhibit a potent repellent activity against blood-sucking and biting insects, ticks and mites, including *Aedes aegypti*—a mosquito vector responsible for transmission of disease agents such as dengue fever and the Zika virus. A combination of reverse phase chromatography and mass spectrometry revealed that the active fraction contained two modified peptides identical to previously reported peptides called "xenoGUFamines" (See Sebastian W. Fuchs (2013), "Investigation of the biosynthesis of bacterial natural products," PhD dissertation, Johann Wolfgang Goethe University, pp. 76-96.) The repellent activity is comparable to or better than that of DEET in side-by-side assays. Thus, disclosed and claimed herein are a novel class of compounds for use as active ingredients in arthropod repellent compositions, as well as methods of using the active ingredients and compositions containing one or more of them to repel arthropods, including blood-sucking and biting insects, ticks and mites.

Specifically disclosed herein is a composition for repelling blood-sucking and biting insects, ticks and/or mites. The composition comprises an amount of one or more compounds of Formula I:

wherein R is selected from a 5-membered or 6-membered carbon-containing ring, having zero, one, two, or three double bonds, and having zero, one, two, or three heteroatoms, wherein the one, two, or three heteroatoms, if present, are selected from nitrogen, oxygen, and sulfur; "x" is an integer from 0 to 5; and "y" is an integer from 1 to 10; or a salt thereof. The compound is disposed in a liquid, solid, or semi-solid topical delivery vehicle. The amount of the compound disposed in the topical delivery vehicle is sufficient to yield a concentration of the compound that is repellent to blood-sucking and biting insects, ticks and/or mites.

More specific versions of the composition include those where the active compound is one in which "x" is 0, 1, or 2, "y" is 1 to 5; and if one or more heteroatoms are present in substituent R, the heteroatoms are all nitrogen. Thus, R may be selected from pyrrolidinyl, 3-pyrrolinyl, 2-pyrrolinyl, 2H-pyrrolyl, 1H-pyrrolyl, pyrazolidinyl, imidazolidinyl, 2-pyrazolinyl, 2-imidazolinyl, pyrazolyl, imidazolyl, 1,2,4-triazolyl, 1,2,3-triazolyl, phenyl, piperidinyl, pyridinyl, piperazinyl, pyridazinyl, pyrimidinyl, pyrazinyl, 1,2,4-triazinyl, and 1,3,5-triazinyl.

In a still more specific version of the composition, R is phenyl or imidazolyl. More specifically still a compositions containing a compound of Formula I in which R is phenyl or 4-imidazolyl, and the subscript "y" is 4.

Likewise disclosed herein is a method for repelling blood-sucking and biting insects, ticks and mites, said method comprising treating an object or area with a composition comprising a blood-sucking and biting insect, tick and/or mite repellent-effective amount of at least one compound of Formula I:

zolidinyl, imidazolidinyl, 2-pyrazolinyl, 2-imidazolinyl, pyrazolyl, imidazolyl, 1,2,4-triazolyl, 1,2,3-triazolyl, phenyl, piperidinyl, pyridinyl, piperazinyl, pyridazinyl, pyrimidinyl, pyrazinyl, 1,2,4-triazinyl, and 1,3,5-triazinyl. The R substituent may be selected from phenyl or imidazolyl. Preferred compounds for use in the method include those in which R is phenyl or 4-imidazolyl, and "y" is 4.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more."

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in the field of arthropod-repellent compositions.

wherein R is selected from a 5-membered or 6-membered carbon-containing ring, having zero, one, two, or three double bonds, and having zero, one, two, or three heteroatoms, wherein the one, two, or three heteroatoms, if present, are selected from nitrogen, oxygen, and sulfur; "x" is an integer from 0 to 5; and "y" is an integer from 1 to 10; or a salt thereof. An amount of the compound is preferably (optionally) disposed in a topical delivery vehicle to yield a concentration of the compound that sufficient to repel blood-sucking and biting insects, ticks and/or mites.

As noted previously, in the method a compound may be used in which "x" is 0, 1, or 2, "y" is 1 to 5; and the heteroatom(s) if present in R is nitrogen. The R substituent may be selected from (but is not limited to) pyrrolidinyl, 3-pyrrolinyl, 2-pyrrolinyl, 2H-pyrrolyl, 1H-pyrrolyl, pyra-

BRIEF DESCRIPTION OF THE FIGURES

Five peaks are shown, labeled I, Is, II, III and IV. The peak labeled "III*" in FIG. 4 was found to be the most repellent.

DETAILED DESCRIPTION

Abbreviations and Definitions:

Unless defined otherwise, all technical and scientific terms used herein have the same meaning as commonly understood by one of ordinary skill in the art of arthropod-repellent compositions intended for application to human skin. The term "about" is defined as plus or minus ten percent; for example, about 100° C. means 90° C. to 110° C.

The terms "object" or "area" are defined to include (without limitation) any place where the presence of the target pests (e.g., mosquitoes) is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth; also includes the outer covering of a living being, such as skin, fur, hair, or clothing. The method disclosed herein includes dispensing the compounds and compositions described into the environment in vapor form (for example, as an aerosol) preferably using devices that allow a slow sustained release of the compounds into the environment or onto the skin and/or clothing of a human from a sealed canister.

The term "heterocycle" as used herein means a cyclic moiety comprised principally of carbon atoms, but having 1, 2, or 3 non-carbon atoms selected nitrogen, oxygen, and/or sulfur. A very large number of heterocyclic moieties are well known. For example, a non-limiting list of nitrogen-containing heterocycles includes:

and the like.

Analogous oxygen-containing, sulfur-containing, and mixed-heteroatom heterocyclic moieties include tetrahydrofuran, furan, 1,3-dioxolane, tetrahydrothiophene, thiophene, oxazole, isoxazole, isothiazole, thiazole, 1,2-oxathiolane, 1,3-oxathiolane, 1,2,5-oxadizaole, 1,2,3-oxdaizole, 1,3,4-thiadiazole, 1,2,5-thiadiazole, sulfolane, tetrahydropyran, 2H-pyran, 4H-pyran, 1,4-dioxolane, 1,4-dioxine, thiane, 2H-thiopyran, 4H-thiopyran, 1,3-dithiane, 1,4-dithiane, 1,3,5-trithiane, morpholine, 1,2-oxazine (2H-, 4H-, and 6H-), 1,3-oxazine (2H-, 4H-, and 6H-), 1,4-oxazine (2H- and 4H-), thiomorpholine, 1,2-thiazine (2H- and 4H-), 1,3-thiazine (2H- and 4H-), 1,4-thiazine (2H- and 4H-), and the like.

Xenorhabdus spp.:

The repellent compounds disclosed herein were isolated from culture supernatants of wild-type *Xenorhabdus budapestensis*, DSM Accession No. 16342 (Deutsche Sammlung von Mikroorganismen and Zellkulturen GmbH ("DSMZ") [German Collection of Microorganisms and Cell Cultures] InhoffenstraBe 7B, 38124 Braunschweig, Germany), hereinafter "Xbu." The same species is also deposited publicly as OP 108891 (Collection d'Institut Pasteur, Paris, France) and NCIMB 14016 (National Collection of Industrial Food and Marine Bacteria, Aberdeen, Scotland). Xbu is a bacterium that infects nematodes. Others species of the genus *Xenorhabdus* likely produce the same compounds and can be used to isolate the active ingredients disclosed herein. Included among the genus of *Xenorhabdus* that are suitable for isolating the compounds disclosed herein include *Xenorhabdus beddingii*, *Xenorhabdus bovienii*, *Xenorhabdus cabanillasii*, *Xenorhabdus doucetiae*, *Xenorhabdus ehlersii*, *Xenorhabdus griffiniae*, *Xenorhabdus hominickii*, *Xenorhabdus indica*, *Xenorhabdus innexi*, *Xenorhabdus ishibashii*, *Xenorhabdus japonica*, *Xenorhabdus khoisanae*, *Xenorhabdus koppenhoeferi*, *Xenorhabdus kozodoii*, *Xenorhabdus magdalenensis*, *Xenorhabdus mauleonii*, *Xenorhabdus miraniensis*, *Xenorhabdus nematophila*, *Xenorhabdus poinarii*, *Xenorhabdus romanii*, *Xenorhabdus stockiae*, *Xenorhabdus szentirmaii*, and *Xenorhabdus vietnamensis*.

Samples of these species are commercially available from many culture collections, including DSMZ and ATCC (formerly the American Type Culture Collection, 10801 University Boulevard, Manassas, Va. 20110 USA). See, for example, ATCC® 49542, ATCC® 35272, ATCC® BAA-2406, ATCC® 19061, ATCC® 35271, ATCC® 49122, ATCC® 49109, ATCC® 700168, ATCC® BAA-2153, ATCC® 39497, ATCC® 49121, ATCC® 49110, ATCC® 33569, ATCC® BAA-2478, and ATCC® 53200. See also *Xenorhabdus beddingii*, DSM-4764; *Xenorhabdus beddingii*, DSM-4765; *Xenorhabdus bovienii*, DSM-4766; *Xenorhabdus budapestensis*, DSM-16342; *Xenorhabdus cabanillasii*, DSM-17905; *Xenorhabdus doucetiae*, DSM-17909; *Xenorhabdus eapokensis*, DSM-104079; *Xenorhabdus ehlersii*, DSM-16337; *Xenorhabdus griffiniae*, DSM-17911; *Xenorhabdus hominickii*, DSM-17903; *Xenorhabdus indica*, DSM-17382; *Xenorhabdus indica*, DSM-17383; *Xenorhabdus indica*, DSM-17384; *Xenorhabdus indica*. DSM-17906; *Xenorhabdus indica*, DSM-26379; *Xenorhabdus innexi*, DSM-16336; *Xenorhabdus ishibashii*, DSM-22670; *Xenorhabdus japonica*, DSM-16522; *Xenorhabdus khoisanae*, DSM-25463; *Xenorhabdus khoisanae*, DSM-26373; *Xenorhabdus khoisanae*, DSM-26374; *Xenorhabdus khoisanae*, DSM-26378; *Xenorhabdus koppenhoeferi*, DSM-18168; *Xenorhabdus kozodoii*, DSM-17907; *Xenorhabdus magdalenensis*, DSM-24915; *Xenorhabdus mauleonii*, DSM-17908; *Xenorhabdus miraniensis*, DSM-17902; *Xenorhabdus nematophila*, DSM-3370; *Xenorhabdus* DSM-4768; *Xenorhabdus romanii*, DSM-17910; *Xenorhabdus stockiae*, DSM-17904; *Xenorhabdus szentirmaii*, DSM-16338; *Xenorhabdus thuongxuanensis*, DSM-104078; and *Xenorhabdus vietnamensis*, DSM-22392.

Cultivation of *Xenorhabdus* spp. is straightforward. DSMZ recommends culturing at 30° C. in a culture medium containing:

| | |
|---|---|
| Peptone from casein | 15.0 g |
| Peptone from soymeal | 5.0 g |
| NaCl | 5.0 g |
| Agar | 15.0 g |
| Distilled water | 1000.0 mL |

Adjust pH to 7.3.

An alternative set of conditions is to culture at 28° C. in a culture medium containing:

| | |
|---|---|
| Trypticase Soy Broth | 30.0 g |
| Agar | 15.0 g |
| Distilled water | 1000.0 mL |

Adjust pH to 7.3

The repellent compounds can then be isolated from the culture supernatant as described below.

Product Isolation:

The compound wherein R is phenyl or imidazolyl, "x" is 0, 1, or 2, and "y" is 4 can be isolated from the culture supernatant of cultured *Xenorhabdus* spp., preferably Xbu. The *Xenorhabdus* spp. are cultured as described hereinabove. The active ingredient is then separated from the culture supernatant using reversed-phase flash chromatography or reversed-phase preparative-scale HPLC using a C18 column as described in Sebastian Fuch's 2013 doctoral dissertation "Investigation of the biosynthesis of bacterial natural products," Johann Wolfgang Goethe University. See also Fuchs et al (2012) "Neutral loss fragmentation pattern-based screening for arginine-rich natural products in *Xenorhabdus* and *Photorhabdus*," Anal. Chem. 84(16):6948-6955.

Briefly, a reversed phase-solid-phase extraction strategy using a C18 column employing stepwise elution with 10, 20, 30% ACN/0.1% TFA, separates bicornutin A (which elutes with 10% ACN/0.1% TFA) from the subject class of repellent-active compounds, which elute at 20% ACN/0.1% TFA and 30% ACN/0.1% TFA (data not shown). A host of suitable, commercially C18 columns can be used for this purpose, including Phenomenex' Strata C18E (Phenomenex, Inc. Torrance, Calif.).

The structure of the purified compounds can be confirmed by means of 1-D and 2-D NMR spectroscopy. A 4.5 mg sample of the compound(s) are dissolved in 600 μl $H_2O/D_2O$ (9:1) at 286 K and analyzed using any suitable NMR instrument (e.g., a Bruker AVANCE 500 spectrometer operating at a proton frequency of 500.30 MHz and a $^{13}$C-carbon frequency of 125.82 MHz).

Formula I

Figure 4:
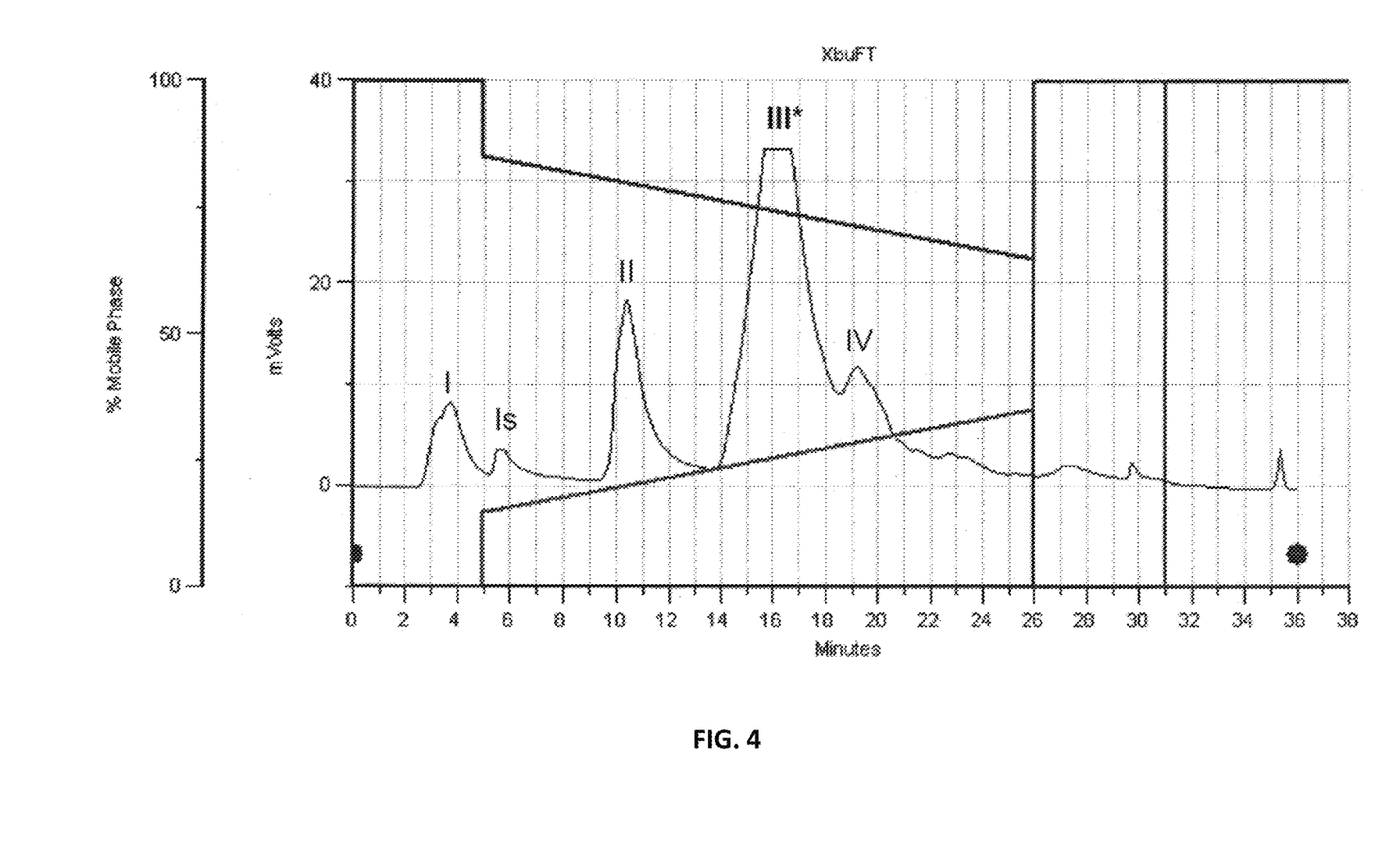
FIG. 4 is a HPLC elution profile using an analytical reverse-phase C18 column of the peak depicted in FIG. 2.

The compound of Formula I in which R is phenyl, "x" is 2 and "y" is 4 has been dubbed "xenoGUFamine Ia." (See FIG. 4.2.2.a of the Fuchs dissertation, at page 71.). The structure of xenoGUFamine Ia encompasses a N-terminal peptide backbone with the primary structure γAsp-Phe-Asn-Asn-Thr-Pro, where the side chains of the first Asn and the Thr residue are dehydratively macrocyclized via a peptide bond.

Based on the structure of xenoGUFamine Ia, the structures of several other structurally related xenoGUFamine derivatives in which "R" is imidazolyl or phenyl, "x" is 0, 1, or 2, and "y" is 4 have been elucidated by means of MALDI-HCD-MS$^2$ (that is, matrix-assisted laser desorption/ionization higher-energy collisional dissociation tandem mass spectrometry) (data not shown).

De Novo Synthesis:

The compounds disclosed herein, because they contain peptide bonds and are thus proteinaceous in nature, can also be fabricated de novo using well-known solid- or solution-phase polypeptide synthesis. Such procedures include both solution- and solid-phase procedures, e.g., using both Boc and Fmoc methodologies. Thus the subject polypeptides may be prepared by successive amide bond-forming procedures in which amide bonds are formed between an amino group of a first amino acid residue or analog thereof and a carboxyl group of a second amino acid residue or analog thereof. The amide bond-forming step may be repeated as many times, and with specific amino acid residues or precursors thereof as required to give the desired final polypeptide. Solid-phase and liquid-phase methods of linking amino acid monomers to yield polypeptides are well known and will not be discussed in detail. See, for example, "Peptide Synthesis and Applications, $2^{nd}$ Ed." K. J. Jensen, A. P. Tofteng, and S. L. Peterson (Eds.), ISBN-13: 978-1627035439, © 2013 Humana Press, Totowa, N.J. USA; "Fmoc Solid Phase Peptide Synthesis: A Practical Approach," W. C. Chan and Peter D. White (Editors) ISBN-13: 978-0199637249, © 2000 Oxford University Press, Inc. NY, USA. Methods for fabricating macrocyclic peptides are described in the relevant scientific literature. See, for example, Cohrt and Nielsen (2014) "Solid-Phase Synthesis of Peptide Thioureas and Thiazole-Containing Macrocycles through Ru-Catalyzed Ring-Closing Metathesis," *ACS Comb. Sci.* 16(2): 71-77; Chung, White and Yudin (2017) "Solid-phase synthesis, cyclization, and site-specific functionalization of aziridine-containing tetrapeptides," Nature Protocols 12: 1277-1287; and Baptiste, Douat-Casassus, Laxmi-Reddy, Godde, Huc (2010) "Solid Phase Synthesis of Aromatic Oligoamides: Application to Helical Water-Soluble Foldamers," *J. Org. Chem.* 75(21): 7175-7185.

Repellent Compositions:

The compounds, which can be used in undiluted or diluted form, can be formulated into repellent compositions as is well known in the repellent, cosmetic, and pesticide fields. Thus, the compounds may be formulated in the form of solutions, suspensions emulsions, gels, ointments, pastes, creams, powders, sticks, sprays or aerosols from spray containers. The compounds can be incorporated, for example, into granules, oily spraying agents or slow-release formulations.

The formulations are prepared in a known manner by mixing or diluting the compounds with one or more solvents, diluents or carriers. Useful solvents/diluents include water, methanol, ethanol, xylene, chlorobenzenes, paraffins, and the like. Carriers include, for example, kaolins, aluminas, talc, chalk, highly disperse silicic acid and silicates, nanoclays, and the like. Emulsifying agents include polyoxyethylene fatty acid esters, polyoxyethylene fatty alcohol ethers, alkylsulphonates and arylsulphonates, and the like. Dispersing agents include lignin, methylcellulose, and the like.

One or more compounds disclosed herein can be mixed with one another in the formulations or one or more compounds disclosed herein can also be used as mixtures with other known active compounds (for example sunscreen agents, DEET, picarin, etc.). The formulations in general contain between about 0.01 wt % and 5 wt % of active compound, preferably between about 0.1 wt and about 3% (e.g., 0.5-90%).

For protection from mosquitoes, the compounds are generally either applied to human or animal skin, or items of clothing and other objects are treated with the compounds. Preferably, the compounds are dispensed into the environment (e.g., outdoors or indoors) in vapor form (e.g., an aerosol).

The compounds are also suitable as an additive to impregnating agents, for example, textile webs, articles of clothing and packaging materials, and as an additive to polishing, cleaning and window-cleaning agents.

The compositions contain a carrier and the compound. The repellent is generally applied with a carrier component. The carrier component can be a liquid material, a solid material. As is known in the art, the vehicle or carrier to be used refers to a substrate such as a gel, polymers, or the like. All of these substrates have been used to release insect repellents and are well known in the art.

The compounds herein are described as repellents because they result in a reduction in the ability of mosquitoes to locate a host, and thus reduce the incidence of biting. Generally, an insect repellant is any compound or composition which deters insects from a host, thus the term "repelling" is defined as causing insects to make oriented movements away from a source of a chemical repellent. (See, for example, Dethier, V. L., et al., *J. Econ. Ent.*, 53: 134-136 (1960).) "Repelling" also includes inhibiting feeding by mosquitoes when a chemical is present in a place where mosquitoes would, in the absence of the chemical, feed. Thus the term "repelling" also includes reducing the number of insect bites on a treated area or object (e.g., mammalian skin which has been treated topically with the compositions or compounds) when compared to the same area or object which is untreated.

The amount of the compound used will be at least an effective amount. The term "effective amount," as used herein, means the minimum amount of the compound needed to reduce the ability of mosquitoes, ticks, mites, etc. to locate a host and thus reduce the incidence of biting, or to cause mosquitoes, ticks, mites, etc. to make oriented movements away from a treated area or object as compared to the same area or object which is untreated. The term "effective amount," as used herein, also means the minimum amount of the compound needed to reduce the number of insect bites on a treated area or object when compared to the same area or object which is untreated. Effective concentrations of the compound in the compositions may vary between about 0.01 and about 95 wt %, preferably between about 0.01 and about 5 wt %. The precise amount needed will vary in accordance with the particular repellent composition used; the type of area or object to be treated; the number of hours or days of repelling needed; and the environment in which the area or object is located. The precise amount of repellent can easily be determined by one skilled in the art given the teaching of this application. See the Example for suitable procedures.

The compounds may be used with other repellents or mosquito control agents, for example insecticides. When used, these agents should be used in an amount which, as readily determined by one skilled in the arts, will not interfere with the effectiveness of the compound.

Testing for Repellency:

Repellency screening tests for experimental chemicals were carried out to identify candidates that might be useful repellents. The repellent efficacy was compared to that of the standard repellent, DEET. Experimental compounds were assessed at a range of concentration to determine the minimum effective dosage (MED) which was the concentration threshold of where the repellent began to fail and allowed bites. This was done using the apparatus shown in FIG. 1. See the Examples, below, for details. Putative repellents may also be tested at a predetermined concentration over a selected time period.

Minimum Effective Dosage (MED) Test: The MED bioassays on treated cloth is a method of screening to determine the minimum amount of a repellent needed to prevent bites. Experimental compounds were prepared in solution and serially diluted (see Example). The standard repellent N,N-diethyl-3-methylbenzamide (DEET) was also tested at the same concentration levels to serve as a control and a comparison for relative repellency.

Complete Protection Time Test: A complete protection time (CPT) on treated cloth is another method of screening used to determine the repellent duration of experimental chemicals that have not yet been determined to be safe for use on humans. The standard repellent DEET was used as a positive control as a benchmark by which to compare the repellents. Experimental compounds were prepared in solutions of known concentrations. The same concentration level of DEET was also prepared in this way to serve as a control and also as a comparison for relative repellency.

Arthropods Repelled:

The compositions and compounds are useful for repelling a host of harmful or troublesome blood-sucking and biting insects, ticks and mites, including mosquitoes. Among the organism repelled by the subject compounds are (by way of example and not limitation) *Aedes, Culex* and *Anopheles* species including but not limited, *Aedes aboriginis, Aedes aegypti, Aedes albopictus, Aedes cantator, Aedes sierrensis, Aedes sollicitans, Aedes squamiger, Aedes sticticus, Aedes vexans, Anopheles quadrimaculatus, Culex pipiens,* and *Culex quinquefasciatus*), sand flies (for example *Phlebotomus* and *Lutzomyia* species), bed bugs (for example *Cimex lectularius*), biting midges (*Culicoides* sp.), blackflies or buffalo gnats (*Simulium* sp.), biting flies (for example *Stomoxys calcitrans*), tsetse flies (*Glossina* sp.), horseflies (*Tabanus, Haematopota* and *Chrysops* species), house flies (for example *Musca domestica* and *Fannia canicularis*), meat flies (for example *Sarcophaga carnaria*), flies which cause myiasis (for example *Lucilia cuprina, Chrysomyla chloropyga, Hypoderma bovis, Hypoderma lineatum, Dermatobia hominis, Oestrus ovis, Gasterophilus intestinalis,* and *Cochliomyia hominovorax*), bugs (for example *Cimex lectularius, Rhodnius prolixus,* and *Triatoma infestans*), lice (for example *Pediculus humanus, Haematopinus suis,* and *Damalina ovis*), louse flies (for example *Melaphagus orinus*), and fleas (for example *Pulex irritans, Ctenocephalides canis,* and *Xenopsylla cheopis*), sand fleas, and blood-feeding ticks (for example, *Ornithodorus moubata, Ixodes ricinus, Ixodes scapularis, Boophilus microplus, Amblyomma americanum,* and *Amblyomma hebreum,* and mites such as *Sarcoptes scabiei* and *Dermanyssus gallinae*).

EXAMPLES

The following examples are intended only to further illustrate the invention and are not intended to limit the scope of the invention as defined by the claims.

Figure 1:
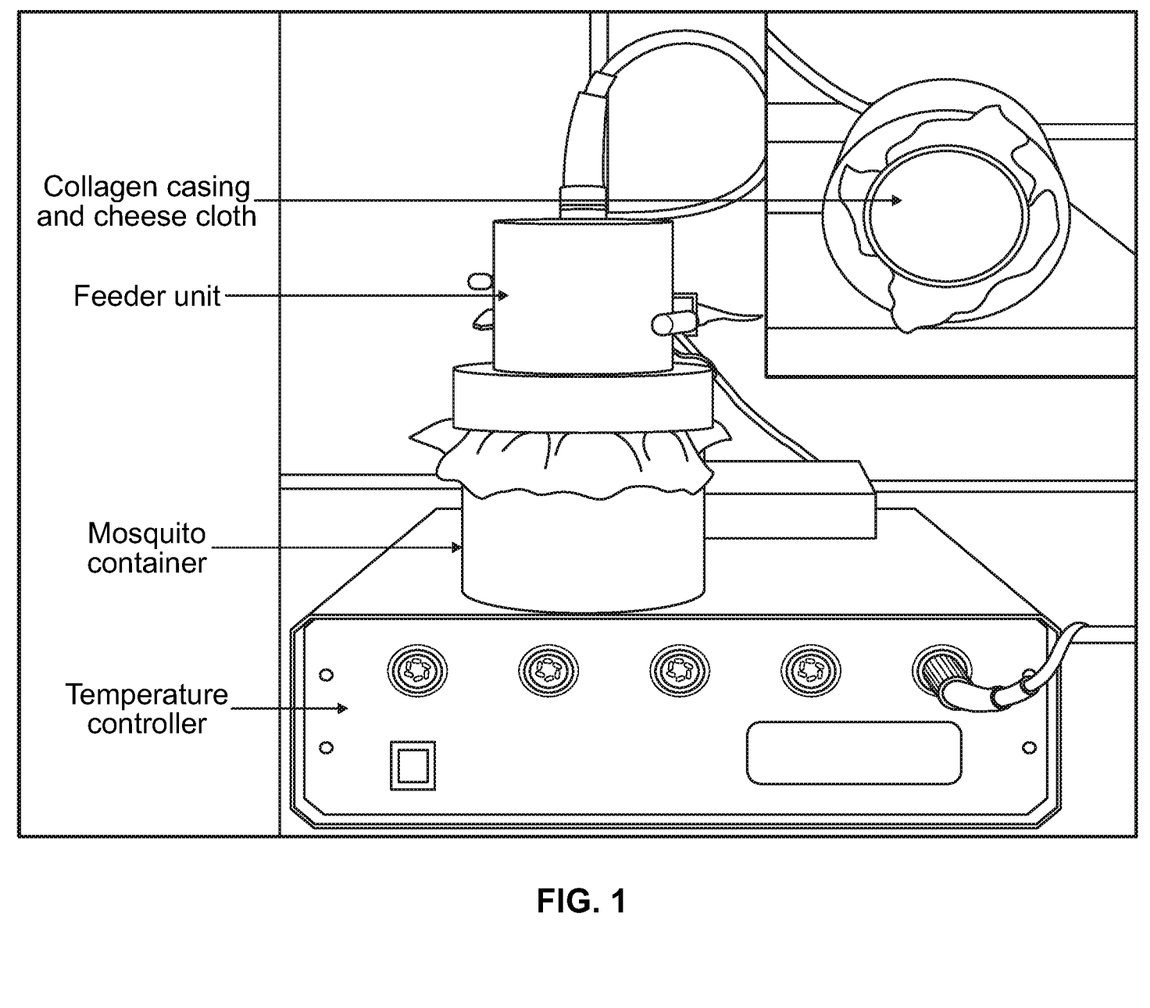
FIG. 1 is a photograph of the equipment used for the repellent screening assay.

To measure the effectiveness of any given repellent disclosed herein, an apparatus as shown in FIG. 1 may be used. FIG. 1 is a photograph of the equipment used for the repellent screening assay. The apparatus includes a temperature-controlled feeder unit which includes a collagen casing covered by conventional cheese cloth. The collagen mimics the surface of human and is in contact with a heating element (not seen in FIG. 1) whose temperature is controlled by the temperature controller. The collagen pad is saturated with a solution that mimics human blood. The compound whose repellency is to be tested is applied to the cheese cloth, which is then affixed to the collagen pad. In the main panel in FIG. 1, the feeder unit is shown in its operational position, on top of a container in which are mosquitos (or any other arthropod) that is to be repelled. The inset in FIG. 1 shows the inside of the feeder unit which contains the collagen pad covered by the cheesecloth. In practice, a known amount of putative repellent is applied to the cheese cloth. Unfed mosquitos, for example, are within the mosquito container. The feeder unit is then placed on top of the mosquito container for a pre-determined amount of time. The mosquitos are then sacrificed and examined to determine how many mosquitos fed (i.e., were not repelled) and how many mosquitos were still unfed after the test (i.e, were repelled). In this fashion, very reliable data can be generated regarding the effectiveness of any putative repellent composition. See Katritzky, A. R., et al. (2008) *Proc. Nat. Acad. Sci. (US)*, 105:7359-7364 and Katritzky, A. R., et al. (2010) *Journal of Med. Entomol.*, 47:924-938.

Figure 2:
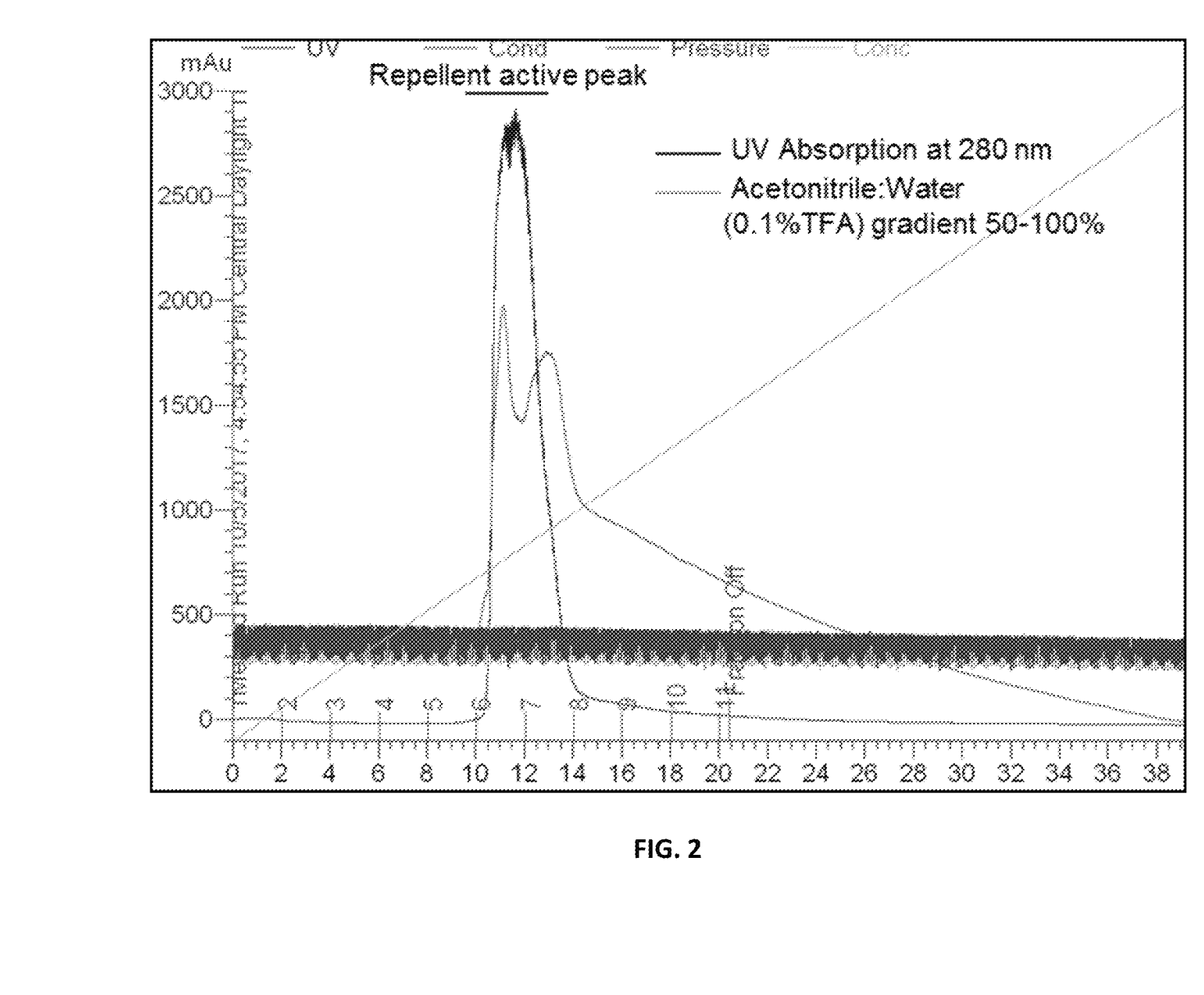
FIG. 2 is a representative chromatogram of elution profiles from Xbu culture supernatants; the repellent active peak is marked.
Figure 3:
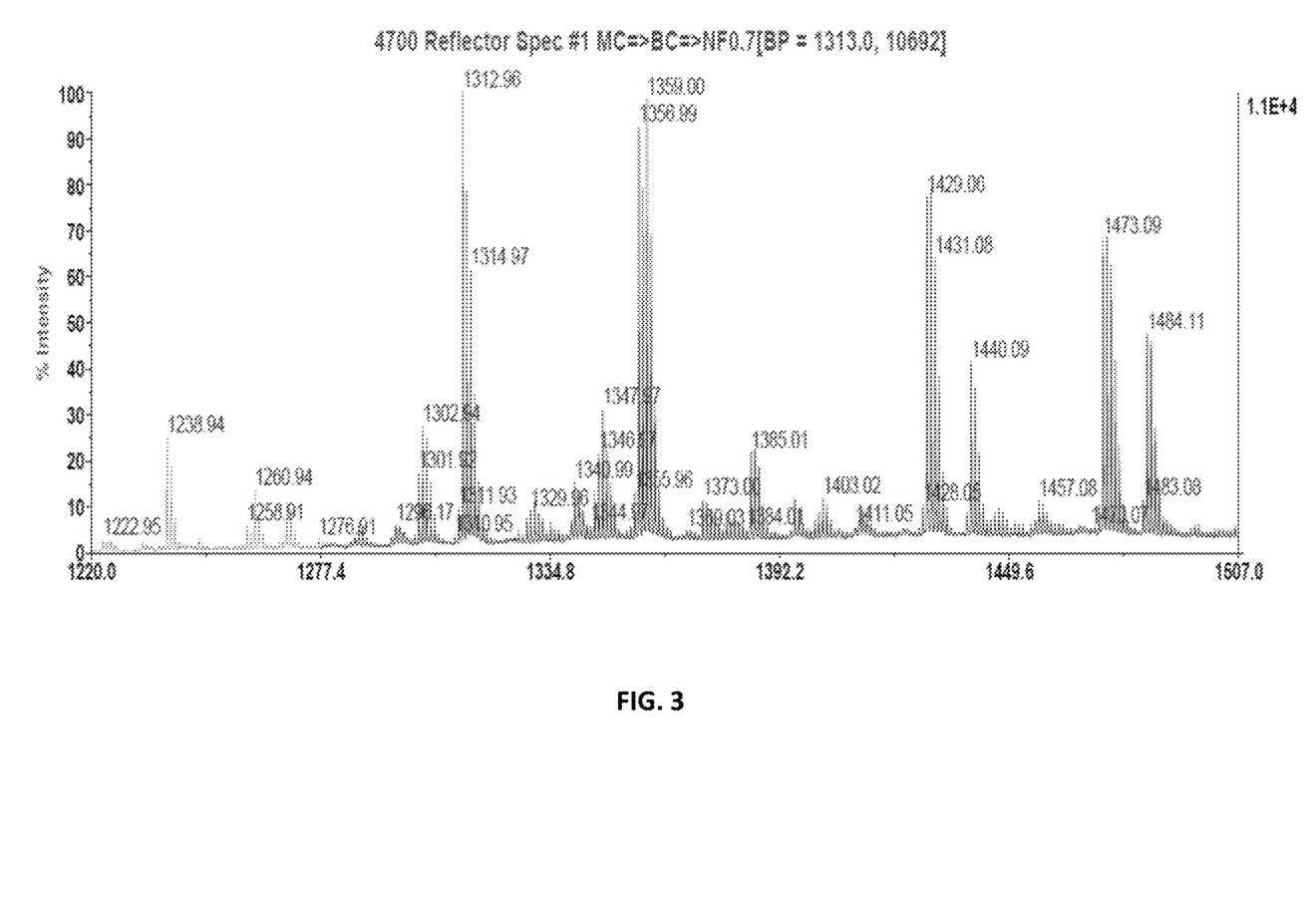
FIG. 3 is a mass-spectrometry spectrum (MADLI-TOF) of the flash chromatography separated repellent active fraction marked in FIG. 2. MALDI-TOF analysis yielded four major masses as seen in the spectrum. The major masses (and related to these) are 1302.94 (1347.96); 1312.96 (1359.00); 1429.06 (1473.09) and 1440.09 (1484.11).

Colonies of Xbu were cultured as described above. The culture medium was then collected and subjected to reversed-phase flash chromatography on a C18 column. Such columns are commercially available from a wide number of suppliers, including ThermoFisher Scientific (Accucore- and Accucore Vanquish-brand C18 columns) (Waltham, Mass.). Thus, FIG. 2 is a representative chromatogram showing elution profiles of flash chromatography column. The repellent active peak is indicated.

Figure 5:
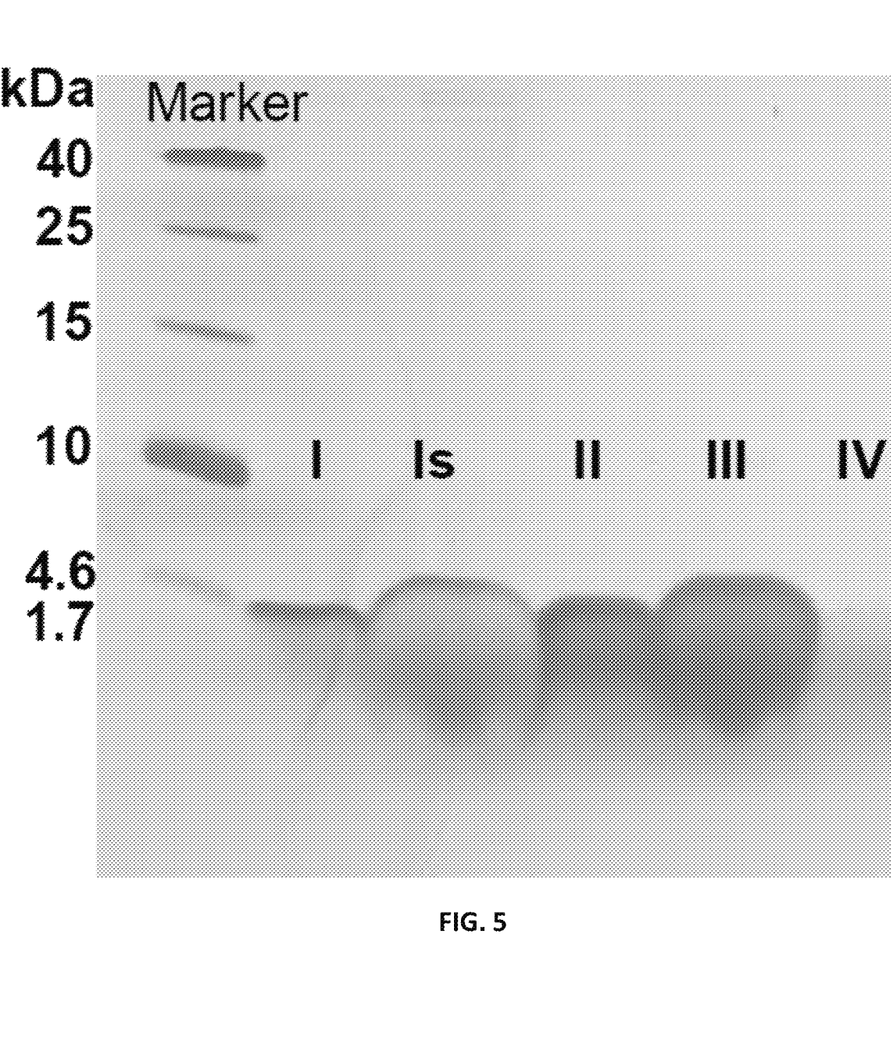
FIG. 5 is a photograph of a silver-stained Tricine-SDS-PAGE gel run on the five eluted fractions shown in the HPLC elution profile depicted in FIG. 4. Marker=Protein molecular weight marker.

The crude fraction isolated as shown in FIG. 2 was tested for its mosquito repellency using the apparatus shown in FIG. 1. It was found to be repellent. (Data now shown). Therefore, the crude fraction was subjected to mass spectrometry to get a better bead on its molecular identify. FIG. 3 presents a representative mass spectrum of the eluate containing the repellent active peak shown in FIG. 2. MALDI-TOF mass spectrum analysis yielded four major masses as seen in the figure. The major masses (and related to these) are 1302.94 (1347.96); 1312.96 (1359.00); 1429.06 (1473.09) and 1440.09 (1484.11).

The repellent active eluate of FIG. 2 was then subjected to a second round of purification, again using C18 reversed-phase chromatography, using HPLC. A representative HPLC chromatogram is depicted in FIG. 4. The chromatogram included elution profiles of four major peaks labeled I, Is, II, III (also called III*) and IV on the image below. Peak labeled III was the most repellent active in testing using the apparatus shown in FIG. 1.

The peaks shown in FIG. 4 were subjected to tricine SDS-PAGE to confirm their molecular weights. The resulting silver-stained gel is shown in FIG. 5. As can be seen from the figure, peaks I, Is, II and III were all reasonably close in terms of molecular weight.

Figure 6:
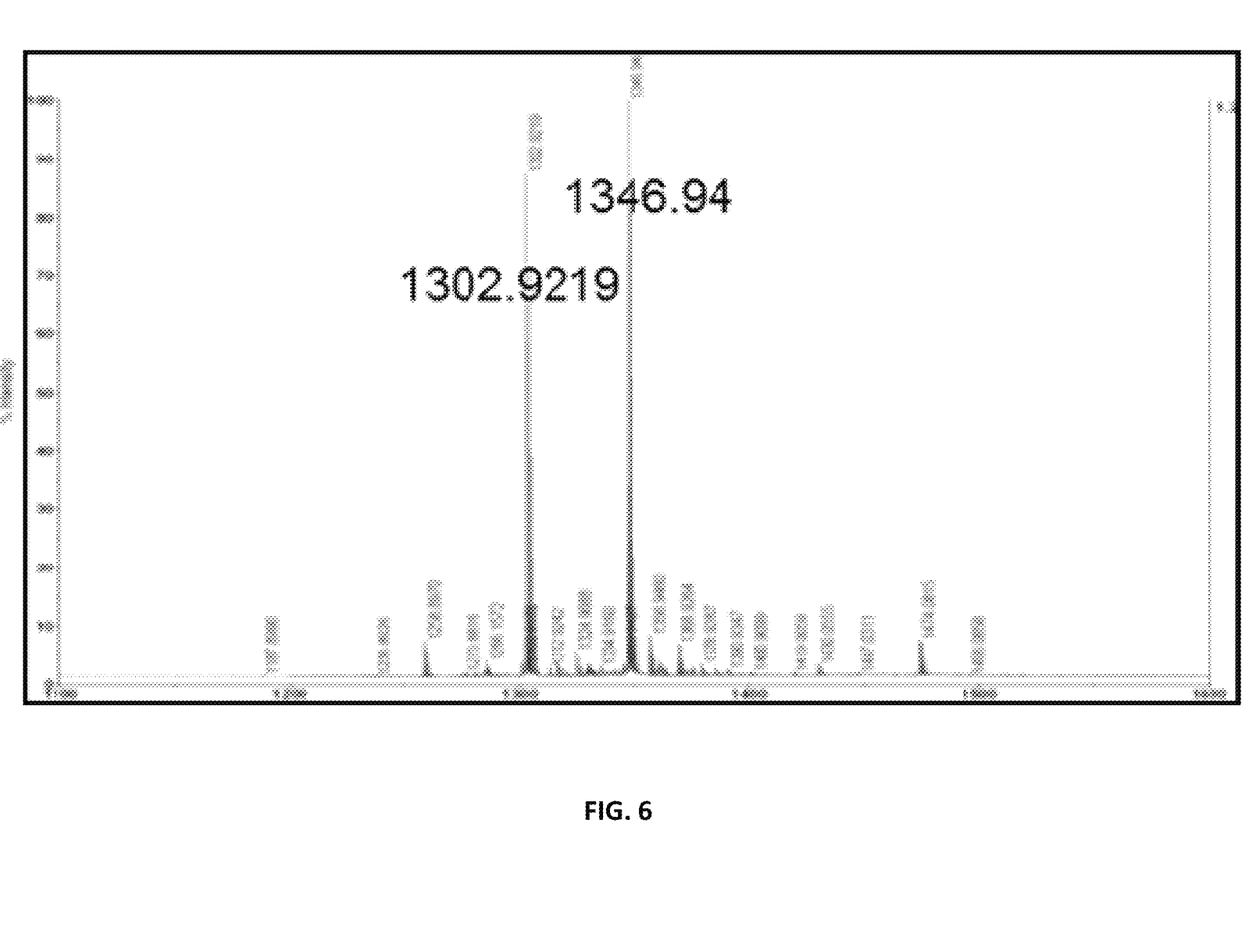
FIG. 6 is a mass-spectrometry spectrum (MALDI-TOF) of HPLC-purified repellent active, peak fraction # III* as shown in FIG. 4. The peak III* fraction contained only two closely related masses, 1302.92 and 1346.95, as seen in the figure.

The HPLC-purified fraction containing peak III was also subjected to mass-spectrometry (MALDI-TOF) analysis. The results are shown in FIG. 6. As can be seen in FIG. 6, the peak III fraction contains only two very closely related masses 1302.92 and 1346.95.

Figure 7:
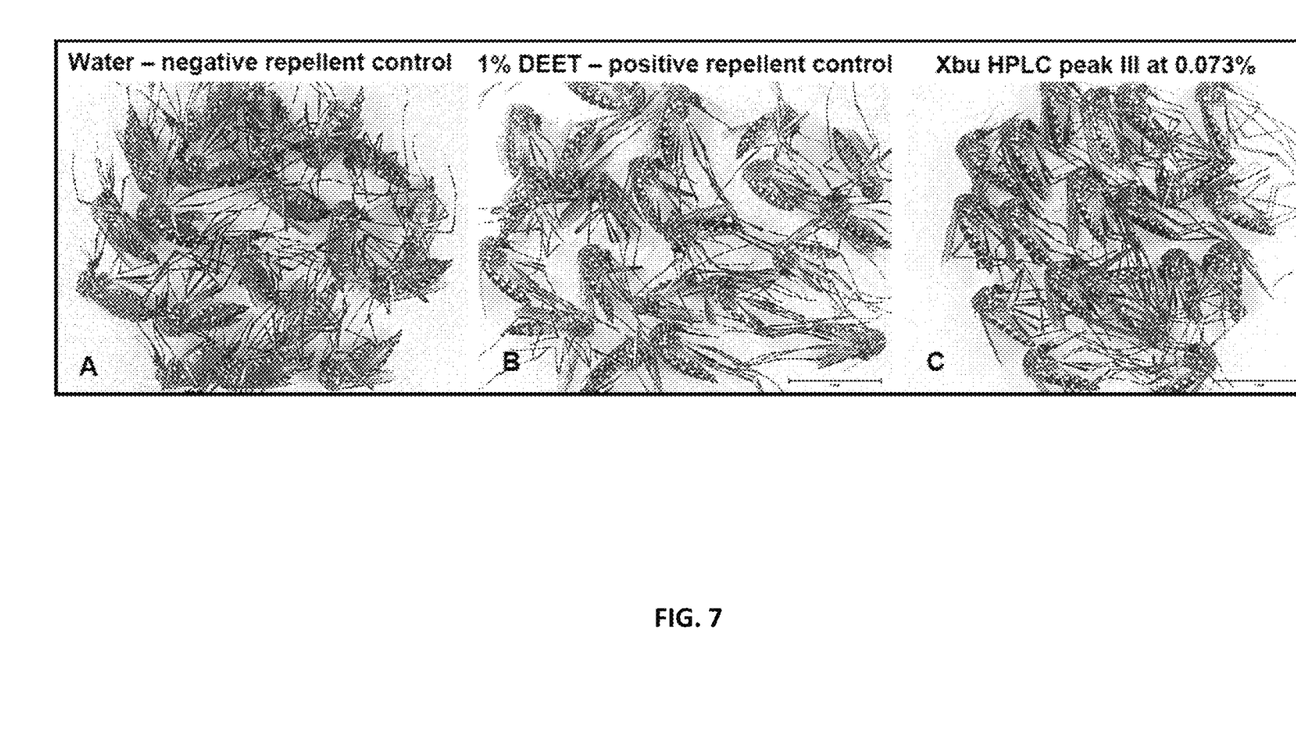
FIG. 7 presents representative images depicting the appearance of fed vs unfed mosquitoes resulting from the repellent screening assay.

In testing the compounds for repellency, candidate compounds are loaded into the apparatus shown in FIG. 1. Unfed mosquitos are then used as test subjects. After the time course of each experiment is completed, the mosquitos are sacrificed and examined to determine how many mosquitos have fed (and thus were not repelled) versus how many mosquitos remain unfed (and thus were repelled). Fed versus unfed mosquitos can be separated by simple visual examination. Fed mosquitoes have an engorged, distended appearance. Representative images depicting the appearance of fed vs unfed mosquitoes resulting from the repellent screening assays is shown in FIG. 7. Images clearly show engorged abdomens and food red dye when mosquitoes were exposed to water only as negative repellent controls (FIG. 7, panel A). Absence of color or engorgement of abdomens indicates no feeding occurred with 1% DEET as a positive control (FIG. 7, panel B) or repellent active Xbu HPLC Peak III fraction at 0.073% (FIG. 7, panel C).

Results for representative repellency testing is shown in Table 1. "RD50" refers to the repellent dose at which 50% of the mosquitoes did not feed; "RD90" refers to the repellent does at which 90% of the mosquitoes did not feed. As can be seen from Table 1, the repellent efficacy of Xbu compared quite favorably with DEET and Picaridin.

TABLE 1

Repellency dose (RD50* and RD90*) comparison between Xbu, Deet and Picaridin against *Aedes aegypti*

| Compound | Goodness-of-fit $\chi^2$ | Pr > ChiSq | Slope ± SE | RD50 | RD90 | RE90¶ |
|---|---|---|---|---|---|---|
| DEET | 5.32 | <.0001 | 1.09 ± 0.35 | 0.012 | 0.188 | 1 |
| Picaridin | 4.46 | <.0001 | 1.73 ± 0.35 | 0.090 | 0.498 | 0.37 |
| Xbu | 3.02 | 0.0002 | 2.08 ± 0.36 | 0.014 | 0.060 | 3.13 |

*RD50 and RD90 - Percent concentration (v/v) of the compound producing 50% or 90% reduction in feeding rate (50 or 90% repellency). RE50 and RE90 (relative efficacy) was derived as a ratio of RD50 and RD90 of DEET to those of Picaridin and Xbu.

Table 2 presents a statistical analysis to determine if the figures presented in Table 1 are significant.

TABLE 2

Comparison* of repellent activity of Xbu with Deet and Picaridin against *Aedes aegypti* Differences of compound Least Squares Means Adjustment for Multiple Comparisons: Tukey-Kramer$^a$

| Compound | Compound | Estimate | S.E. | z Value | Pr > \|z\| | Adj P |
|---|---|---|---|---|---|---|
| DEET | Picaridin | 1.0912 | 0.2944 | 3.71 | 0.0002 | 0.0006 |
| DEET | Peak #3 | 0.1730 | 0.2768 | −0.62 | 0.5320 | 0.8064 |
| Picaridin | Peak #3 | 1.2642 | 0.3097 | −4.08 | <0.0001 | 0.0001 |

*"Proc Probit" averaged values generated using all observations of unfed mosquitoes among replications and three compounds. (SAS/STAT-brand software; SAS Institute Inc., Cary, NC.) The PROBIT procedure within the SAS/STAT software calculates maximum likelihood estimates of regression parameters and the natural (or threshold) response rate for quantal response data from biological assays or other discrete event data.
Repellency comparison among DEET and Picaridin was significant (p < 0.05); DEET and Xbu Peak #3 was not significant (p > 0.05); and Xbu Peak#3 was significantly different from Picaridin (p < 0.05)
$^a$Tukey, John (1949). "Comparing Individual Means in the Analysis of Variance," *Biometrics*. 5(2): 99-114.)
In short, Xbu's repellent activity is on par with that of DEET to a statistically significant degree.

The subject compounds have also been shown to be effective pesticides. See Tables 3 and 4, which reports lethal concentration 50% (LC50) and lethal concentration 90% (LC90) for the peak III compounds against various species of mosquitoes.

TABLE 3

24 h LC50 and 24 h LC90.

| Mosquito | Goodness-of-fit $\chi^2$ | Pr > ChiSq | Slope ± SE | LC50 at 24 h | LC90 at 24 h |
|---|---|---|---|---|---|
| *Aedes aegypti* | 0.9302 | 0.60 | 1.92 ± 0.26 | 5.68 | 26.44 |
| *Anopheles gambiae* | 0.4318 | 0.99 | 7.62 ± 1.41 | 3.46 | 5.10 |
| *Culex pipiens* | 1.42 | 0.041 | 3.08 ± 0.47 | 11.59 | 30.21 |

TABLE 4

48 h LC50 and 24 h LC90.

| Mosquito | Goodness-of-fit $\chi^2$ | Pr > ChiSq | Slope ± SE | LC50 at 48 h | LC90 at 48 h |
|---|---|---|---|---|---|
| *Aedes aegypti* | 1.6850 | 0.0036 | 1.91 ± 0.34 | 2.10 | 9.82 |
| *Anopheles gambiae* | IE* | IE | IE | IE | IE |
| *Culex pipiens* | 0.73 | 0.88 | 3.88 ± 0.51 | 4.51 | 9.65 |

*IE = inestimable data as all of the Anopheles gambiae larvae died at concentrations tested Rearing and Maintenance of Mosquitoes:

A colony of the *Aedes aegypti* Liverpool strain was maintained at the University of Wisconsin according to standard procedures reported previously (Paskewitz et al., 1999; Kajla et al., 2010, Christensen et al., 1984). *Anopheles gambiae* and *Culex pipiens* (Iowa strain) were reared according to established protocols (Aliota et al., 2016) in a 100 square feet walk-in environmental chamber maintained at 26.5±0.5° C. and 80±5% relative humidity. For egg production, adult female mosquitoes were offered defibrinated rabbit blood (HemoStat Laboratories, Dixon, Calif., USA) via a Hemotek-brand membrane feeding system (Discovery Workshops, Accrington, UK) once a week. Adult mosquitoes were maintained on a constant exposure to 10% sucrose on cotton balls and larvae were fed Tetramin®-brand fish food. For repellent assays, nulliparous, mated, twenty 7-10 days old adult female mosquitoes were separated in screened pint-size paper containers (Neptune Paper Products, Fort Lee, N.J., USA). Mosquitoes were starved for 12-16 hours before the repellent assay. Mosquitoes were exposed to repellent compounds for 30 min at room temperature (incandescent light, 25-26° C.) between 10:00 am and 4:00 pm (see below for repellent assay set-up).

Repellent Screening Assay:

Artificial in-vitro feeding systems have been described for screening of repellent compounds. These systems utilize a variation of the following: 1) feeding solution such as blood or artificial diet that mimic blood [Ali et. al, 2017; Huang TH, 2015], 2) a heat source to keep the feeding solution at a constant warm temperature, 3) mosquitoes secured in containers/cages of various dimensions. The heat source is either a water circulator incubator set a particular temperature or a thermostat regulated heat source such as Hemotek-brand heating system. In-vitro feeding systems provide an alternate platform for regular blood feeding for laboratory rearing of mosquitoes as well as for testing of repellents. Such systems eliminate need of human volunteers especially when testing of new repellent compounds of unknown toxicity.

A Hemotek-brand feeding system was used to keep the feeding solution at a constant temperature set at 37° C. A fresh, thoroughly water-washed collagen casing membrane [Nippi edible collagen casing, ViskoTeepak, Kenosha, Wis., USA], and a cocktail diet (Huang TH, 2015) containing 2% food red dye (McCormick & Company Inc., Sparks, Md., USA). The repellent solution for testing was applied to a double layer of cotton cloth (thread count ~44×38 per sq. inch; Joann Fabrics, Madison, Wis.) which was then secured to the Hemotek feeder assembly as shown in Fig. For repellent assays, 1.0 ml of the repellent solution was used to soak the double-layered cheesecloth. For controls, ultrapure water was used. Control feeding assays were conducted with each test repellent assay.

Three replicate feeding experiments were conducted for each assay with mosquitoes hatched from different egg batches to account for cohort bias over a period of three weeks. HPLC-purified, repellent-active fraction was tested at a concentration range of 0.0048% to 0.073% (v/v); DEET and Picaridin at 0.01% to 1.0% (v/v). This range provided 10 to 100% feeding inhibition. DEET was diluted from SC Johnson's OFF! Deep Woods-brand spray bottle repellent (25% DEET), available over-the-counter. Picaridin was obtained from Light and Clean-brand insect repellent (7% picaridin), also available over-the-counter. All test chemicals were diluted in ultrapure water. One replicate of the desired concentration range of a particular compound was tested on the same day. DEET and Picaridin dilutions were tested with half-a-day gap in between tests. The metal feeders were washed extensively with water after every repellent assay. Collagen membrane and feeding were renewed for each exposure test. There was no carryover of the compounds/contamination of the feeders nor inhibition of feeding observed between tests. Bacterial compound was tested purposefully on a different day than the DEET and Picaridin tests as a precaution to avoid any residual interference between assays. Several tests with the repellent HPLC fraction of different batches exhibited consistent, concentration-dependent repellent activity each time tested. The results of three replicate experiments are presented above for each concentration. The total number of mosquitoes tested in the presented data is 60 (total three replicates, n=20/replicate/concentration).

After the assays, mosquitoes were killed by freezing at −20° C. Fed vs unfed mosquitoes were counted under a dissecting microscope. Fed mosquitoes could be easily distinguished from unfed ones. See FIG. 7. Fed mosquitoes were engorged and had red abdomens versus unfed which were lean and no red abdomens. Mosquitoes that were not engorged and had no red color were considered as unfed and hence repelled. This distinction provided a reliable means of assessing the feeding rate of mosquitoes with different compounds and comparisons. Fed versus unfed mosquitoes were counted and the count data used for statistical analysis. Repellent activity was expressed as percent (v/v) dose of the compound that resulted in a 50% or 90% inhibition in mosquito feeding rate (RD50 and RD90; Huang et al., 2015).

Isolation, Purification and Identification of the Repellent Active Compound:

*Xenorhabdus budapestensis* bacteria were maintained as glycerol stocks at −80° C. For culturing, bacteria were streaked on to LB-agar plates containing 0.004% (w/v) triphenyl tetrazolium chloride and 0.025% (w/v) bromothymol blue and 0.1% pyruvate ("LBTA" media). Plates were incubated at 30° C. in the dark for 2-3 days for bacterial colonies to emerge. Culturing on LBTA media allows differentiation between phase I (blue) and phase II (red) bacterial colonies (Fang et al., 2014). Phase I bacteria are reported to primarily secrete secondary metabolites (Boemare N et al., 1988). Thus, a single well-isolated blue colony was selected for further growth in modified minimal medium containing 0.05M $Na_2HPO_4$; 0.05M $KH_2PO_4$, 0.02M $(NH_4)_2SO_4$, 0.001M $MgSO_4$, 0.25% yeast extract and 0.1M glucose. Bacterial cultures (typically 6 flasks of 400 ml each) were grown at 30° C. at 150 rpm in a rotatory shaker and harvested at 72 h post-inoculation via centrifugation (at 4° C., 10,000 rpm, 10 minutes). The chilled, cell-free culture supernatant was mixed with two volumes of ice-cold acetone added in batches of 200 ml while mixing on a magnetic stirrer. The supernatant-acetone mixture was further incubated at 4° C. for 12-16 hours while stirring. Post-precipitation, spent medium/acetone was discarded and precipitated material was air-dried to remove residual acetone. Semi-dried precipitated material containing the repellent active molecules was dissolved in ultrapure water. This solution was then centrifuged at 10,000 rpm to remove undissolved precipitates. The supernatant thus collected was filtered through 0.45µ filter paper and loaded onto a flash reverse-phase c18 column manually (Buchi Corporation, New Castle, Del., USA) using a peristaltic pump. The flash c18 column was then connected to a FPLC (AKTA Prime Plus, GE Healthcare Bio-Sciences, Pittsburgh, USA). HPLC-grade acetonitrile (Fisher Scientific, Madison, Wis., USA) was used for reversed-phase chromatography. All solvents were 0.2µ filtered, and contained 0.1% TFA.

Repellent-active molecules, bound completely to c18, were eluted with a chosen gradient of 50-100% acetonitrile:water/0.1% TFA. A representative image of the elution profile on the flash c18 column (absorbance at 280 nm) is shown in FIG. 2. The peak fractions eluted from the flash column were pooled and lyophilized. The lyophilized material was dissolved in ultrapure water. To get rid of trace amount of higher molecular weights complexes, the purified material was subjected to filtration through centrifugal filters having a 5 kDa nominal molecular weight cutoff (MWCO) (MilliporeSigma, Burlington, Mass., USA). All of the repellent activity was collected in the flow-through fraction (FT fraction) of the 5 kDa MWCO filter. A second reversed-phase analytical column (Vydac-brand c18; Grace, Columbia, Md., USA) was used to separate molecules in the FT fraction via HPLC (Gilson, Inc., Middleton, Wis., USA) over an optimized acetonitrile:water/tfa gradient of 13-40% over 40 min. Multiple HPLC runs were performed to collect sufficient material for downstream repellent assays and mass spectrometry analyses. Pooled peak fractions were subsequently lyophilized. The lyophilized powder was then dissolved in 0.2µ filtered, double-distilled water and stored at −20° C. until tested.

Protein content in the repellent-active fractions was assessed via bicinchoninic acid assays ("BCA") according to the manufacturer's instructions (Pierce BCA Protein Assay Kit, Thermofisher Scientific, Waltham, Mass., USA) as well as total amino acid analysis (Molecular Structure Facility, University of California, Davis, Calif., USA). For visualizing protein/peptide purity during the purification, samples were routinely fractionated on 16% Tricine-SDS gels (Novex Tricine Gel System, ThermoFisher Scientific) and stained via Pierce Silver Stain Kit (ThermoFisher Scientific). The repellent-active fractions were subjected to MALDI-MS analysis at the Mass Spectrometry Facility at the University of Wisconsin-Madison.

Statistical Analysis:

Probit analysis (Statistical Analysis Software, version 9.4; SAS Institute Inc., Cary N.C., USA) was used to analyze repellent and larvicidal activities. Repellent activity (Table 1) was expressed as percent (v/v) dose of the compound (bacterial or DEET or Picaridin) that resulted in a 50% or 90% inhibition in mosquito-feeding rate (RD50 and RD90; Huang et al., 2015). Relative efficacy (RE90) of the repellent activity was derived by dividing RD90 value of the DEET to that of the Picaridin and bacterial compound (Xbu). Least square estimation (Littell et al., 2002) was conducted to compare differences among repellent activity between three compounds based on adjusted p-values (Table 2). Probit analysis was also used to estimate LC50 and LC90 values, the concentration (µg/0.5 ml) of the compound that yielded 50% and 90% larval death at 24 h and 48 h post-exposure respectively (Tables 3 and 4).

Figure 8:
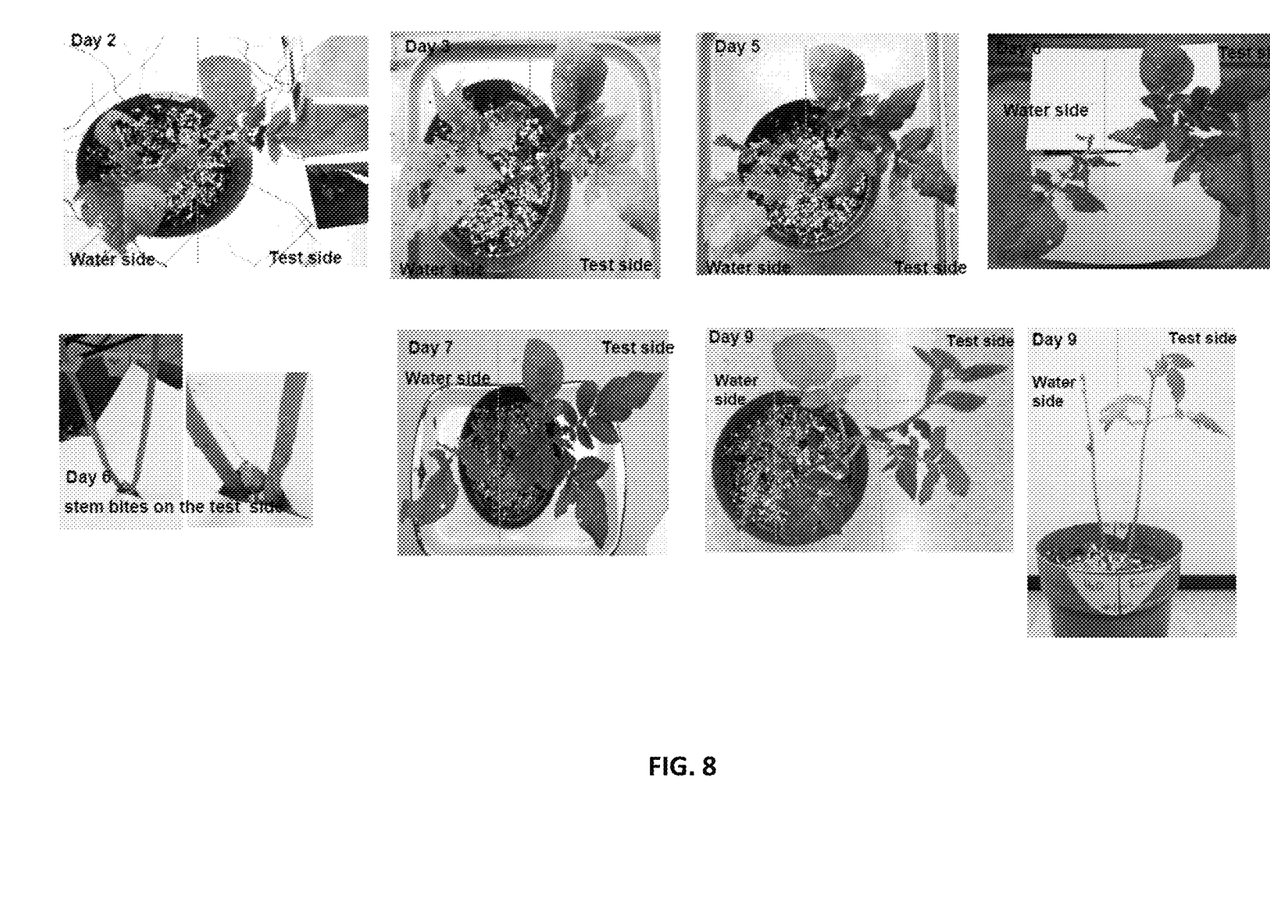
FIG. 8 is a series of photographs taken over the course of 9 days showing a potato plant in which one half of the plant was treated with water (control side) and the other side treated with the repellent composition disclosed herein (test side) and then challenged with 23 Colorado potato plants.

Colorado Potato Bug Repellent:

The compounds disclose herein are effective to repel Colorado potato bugs when sprayed on plants. To demonstrate this activity, 23 Colorado potato bugs were released on Day 1 (D1) onto potato plants that had been sprayed on one half with water (control side) and on the other half with the crude bacterial compound Xbu in water (treated side). The plants were then monitored for nine (9) days. By the 7$^{th}$ day, only 14 insects could be spotted, 13 of which were already dead. A series of photographs of a representative plant, taken over the 9-day course of the study, is shown in FIG. 8. As can be seen from the figure, clearly, the treated of the plant was significantly less probed/eaten as compared to the control side. By Day 9 of the study, one insect remains, on the control side of the plant. No leaves remained on the control side of the plant. The treated side, in contrast, retained its leaves and had no insects present. This experiment shows that the treated leaves were protected from predation by the Colorado potato beetle.

What is claimed is:

1. A method for repelling blood-sucking and biting insects, ticks and mites, the method comprising treating an object or area with a composition comprising a blood-sucking and biting insect, tick and/or mite repellent-effective amount of at least one compound of Formula I:

wherein R is selected from a 5-membered or 6-membered carbon-containing ring, having zero, one, two, or three double bonds, and having zero, one, two, or three heteroatoms, wherein the one, two, or three heteroatoms, if present, are selected from nitrogen, oxygen, and sulfur;

"x" is an integer from 0 to 5; and

"y" is an integer from 1 to 10;

or a salt thereof;

disposed in a liquid, solid, or semi-solid topical delivery vehicle;

wherein the amount of the compound disposed in the topical delivery vehicle is sufficient to yield a concentration of the compound that is repellent to blood-sucking and biting insects, ticks and/or mites.

2. The method of claim 1, wherein "x" is 0, 1, or 2, "y" is 1 to 5; and the heteroatom(s) if present is nitrogen.

3. The method of claim 1, wherein R is selected from pyrrolidinyl, 3-pyrrolinyl, 2-pyrrolinyl, 2H-pyrrolyl, 1H-pyrrolyl, pyrazolidinyl, imidazolidinyl, 2-pyrazolinyl, 2-imidazolinyl, pyrazolyl, imidazolyl, 1,2,4-triazolyl, 1,2,3-triazolyl, phenyl, piperidinyl, pyridinyl, piperazinyl, pyridazinyl, pyrimidinyl, pyrazinyl, 1,2,4-triazinyl, and 1,3,5-triazinyl.

4. The method of claim 1, wherein R is phenyl or imidazolyl.

5. The method of claim 1, wherein R is phenyl or 4-imidazolyl, and "y" is 4.

* * * * *